United States Patent
Feng et al.

(10) Patent No.: US 11,564,625 B2
(45) Date of Patent: Jan. 31, 2023

(54) TISSUE FORCE SENSOR SYSTEMS AND METHODS OF USE

(71) Applicant: Massachusetts Eye and Ear Infirmary, Boston, MA (US)

(72) Inventors: Allen Lee Feng, Cambridge, MA (US); Phillip Changhun Song, Wellesley Hills, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 310 days.

(21) Appl. No.: 16/645,118

(22) PCT Filed: Sep. 11, 2018

(86) PCT No.: PCT/US2018/050457
§ 371 (c)(1),
(2) Date: Mar. 6, 2020

(87) PCT Pub. No.: WO2019/051481
PCT Pub. Date: Mar. 14, 2019

(65) Prior Publication Data
US 2021/0219917 A1    Jul. 22, 2021

Related U.S. Application Data

(60) Provisional application No. 62/556,764, filed on Sep. 11, 2017.

(51) Int. Cl.
*A61B 5/00* (2006.01)
*A61B 90/00* (2016.01)
(Continued)

(52) U.S. Cl.
CPC ............ *A61B 5/6847* (2013.01); *A61B 1/267* (2013.01); *A61B 5/6885* (2013.01); *A61B 90/06* (2016.02);
(Continued)

(58) Field of Classification Search
CPC ...... A61B 1/267; A61B 5/6847; A61B 5/6885; A61B 90/57; A61B 2090/065; A61B 2562/0252
See application file for complete search history.

(56) References Cited

U.S. PATENT DOCUMENTS 4,426,884 A    1/1984 Polchaninoff
4,583,555 A *  4/1986 Malcom ............... A61B 5/103
                                                  600/595
(Continued)

FOREIGN PATENT DOCUMENTS

EP          3351174 A1 *  7/2018  ........... A61B 5/1118

OTHER PUBLICATIONS

Belafsky et al., "Validity and reliability of the Eating Assessment Tool (EAT-10)," Ann. Otol. Rhinol, Laryngol., Dec. 2008, 117(12):919-924.
Corvo et al., "Extra-laryngeal Complications of Suspension Laryngoscopy," Braz. J. Otorhinolatyngol., Nov.-Dec. 2007, 73(6):727-732.
(Continued)

*Primary Examiner* — Daniel L Cerioni
*Assistant Examiner* — Raymond P Dulman
(74) *Attorney, Agent, or Firm* — Fish & Richardson P.C.

(57) ABSTRACT

The disclosure provides tissue force sensor systems and methods for tissues, e.g., laryngeal tissue. The systems include a top housing including on an upper side an attachment mechanism for connecting the top housing to a medical device, e.g., a laryngoscope, and on a lower side a first cavity for receiving a top portion of a force measurement device such as a load cell; a bottom housing including on a lower side an attachment mechanism for connecting the bottom housing to a handle, holding system, or suspension system for holding or supporting the medical device, and on an upper side a second cavity for receiving a bottom portion of the force measurement device; and an attachment device for connecting the top housing to the bottom housing.

15 Claims, 7 Drawing Sheets

(51) Int. Cl.
*A61B 90/57* (2016.01)
*A61B 1/267* (2006.01)

(52) U.S. Cl.
CPC ........ *A61B 90/57* (2016.02); *A61B 2090/065* (2016.02); *A61B 2562/0252* (2013.01)

(56) References Cited

U.S. PATENT DOCUMENTS

| | | | |
|---|---|---|---|
| 5,070,859 A | 12/1991 | Waldvogel | |
| 2006/0047283 A1 | 3/2006 | Evans et al. | |
| 2007/0217199 A1* | 9/2007 | Adam | A61N 5/0616 |
| | | | 362/276 |
| 2008/0294010 A1 | 11/2008 | Cooper | |
| 2010/0094163 A1 | 4/2010 | Deladi et al. | |
| 2013/0123582 A1 | 5/2013 | Xia et al. | |
| 2014/0000361 A1* | 1/2014 | Teixeira | A61B 5/6895 |
| | | | 73/379.01 |
| 2017/0000387 A1* | 1/2017 | Forth | A61B 5/4023 |

OTHER PUBLICATIONS

Feng et al., "Laryngeal Force Sensor: Quantifying Extralaryngeal Complications after Suspension Microlaryngoscopy," Otolaryngol, Head Neck Surg., Aug. 2018, 159(2):328-334.

Jahn et al., "A short history of laryngoscopy," Logoped. Phoniatr. Vocol., Jan. 1996, 21(3-4):181-185.

Orosco et al., "Safety of Adult Ambulatory Direct Laryngoscopy Revisits and Complications," JAMA Otolatynology Head Neck Surg., 2015, 141(8):685-689.

PCT International Preliminary Report on Patentability in International Appln. No. PCT/US2018/50457, dated Mar. 17, 2020, 7 pages.

PCT International Search Report and Written Opinion in International Appln. No. PCT/US2018/50457, dated Nov. 26, 2018, 13 pages.

Rosen et al., "Oropharyngeal complications of suspension laryngoscopy: a prospective study," Laryngoscope, Sep. 2005, 115(9):1681-1684.

Tessema et al., "Tongue paresthesia and dysgeusia following operative microlaryngoscopy," Ann. Otol. Rhinol, Laryngol., Jan. 2006, 115(1):18-22.

* cited by examiner

TISSUE FORCE SENSOR SYSTEMS AND METHODS OF USE

CROSS-REFERENCE TO RELATED APPLICATION

This application is a 371 U.S. National Application of PCT/US2018/050457, filed on Sep. 11, 2018, which claims the benefit of U.S. Provisional Application No. 62/556,764, filed on Sep. 11, 2017. The entire contents of the foregoing applications are hereby incorporated by reference.

TECHNICAL FIELD

This invention relates to procedures that involve the intentional or inadvertent manipulation of tissues, such as procedures using a laryngoscope, and more particularly to detecting and analyzing forces on tissues that arise during such procedures.

BACKGROUND

Many medical procedures involve the manipulation of tissue with a medical device. Often these tissue manipulations are unintended, but are unavoidable during specific medical procedures. For example, direct laryngoscopy (DL) is the most common surgical approach for the removal of vocal fold lesions, both benign and malignant, but can result in unintended manipulation of the tongue and other tissues in the larynx. DL involves placement of a rigid, metal tube, the laryngoscope, into the mouth in line with the vocal folds. Depending on the extent of the surgery, the majority of operations are performed in conjunction with a suspension system and microscope (suspension microlaryngoscopy or SML) as a day procedure (Orosco et al., JAMA Otolaryngol. Head Neck Surg., 141(8):685-9, 2015). These procedures have been the standard practice for laryngeal surgery since the early 1900s, with Killian describing the first instance of SML in 1909 (Jahn et al., Logoped. Phoniatr. Vocol., 21(3-4):181-5, 1996). Since that time, developments and modifications to laryngoscopes have been made, but fundamental methods of suspension are relatively unchanged.

The transoral approach avoids the use of a neck incision, however the laryngoscope places a significant amount of stress and force against the oral cavity, resulting in postoperative tongue pain, numbness, swelling, weakness, dysphagia, and taste alterations. These complications can have significant impacts on quality of life. Current literature suggests a rate of taste alteration occurring in up to 18% of patients (Rosen et al., Laryngoscope, 115(9):1681-4. 2005) with a rate of tongue numbness occurring around 15% of the time (Tessema et al., Ann. Otol. Rhinol. Laryngol., 115(1): 18-22, 2006). Other prospective trials have shown rates of nerve damage around 14% (Corvo et al., Braz. J. Otorhinolaryngol., 73(6):727-32 2007). Many factors have been hypothesized as contributors to these symptoms (time of surgery, mechanical compression, etc.), but no one has thoroughly studied the correlation between mechanical force and compressive symptoms, the amount of pressure required to cause such symptoms, or developed a mechanism to detect these forces.

SUMMARY

The present disclosure describes tissue force sensor (TFS) systems, such as laryngeal force sensor (LFS) systems, and methods of using these systems to provide feedback to users, e.g., surgeons or other operators, on the amount of weight or force being applied to a patient's tissues, such as in the mouth, jaws, tongue, and/or throat during a medical procedure, such as direct laryngoscopy (DL) and other types of surgeries, or during procedures such as endotracheal intubation, e.g., for anesthesia. In general, the new TFSs are safety devices that provide real-time feedback to the user, e.g., operator, during medical procedures. During the procedure, the operator can quantify the forces and impulses delivered to the tissues to reduce pain and post-operative complications.

In one general aspect, the disclosure provides tissue, e.g., laryngeal tissue, force sensor systems that include a top housing including on an upper side thereof an attachment mechanism for connecting the top housing to a medical device, and on a lower side thereof a first cavity for receiving a top portion of a force measurement device; a bottom housing including on a lower side thereof an attachment mechanism for connecting the bottom housing to a handle, holding system, or suspension system for holding or supporting the medical device and on an upper side thereof a second cavity for receiving a bottom portion of the force measurement device; and an attachment device for slidably connecting the top housing to the bottom housing along a central axis of the top and bottom housings, wherein the first and second cavities are sized such that the top and bottom housings do not contact each other when a force measurement device is arranged within the first and second cavities.

In some implementations, the medical device is a laryngoscope and the system is configured to sense force on a laryngeal tissue. In some embodiments, the systems as described herein further include a force measurement device, e.g., a load cell, arranged between the top and bottom housings within the first and second cavities.

In some embodiments, the systems can further include a data acquisition system in communication with the force measurement device and a processor loaded with data analysis software in communication with the data acquisition system. In some implementations of these embodiments, the data acquisition system is configured to receive input signals from the force measurement device and convert those signals into digital output, and wherein the data analysis software is configured to receive the digital output over time and provide real-time force data over time. In certain implementations, the force measurement device is or includes a load cell.

In certain implementations of these systems, the top and/or bottom housings are made of metal, e.g., stainless steel or aluminum.

In some embodiments, the attachment device includes one or more rods that are slidably secured to either the top or bottom housing and fixedly secured to either the bottom or the top housing, wherein the top and bottom housings and rods are arranged such that the top and bottom housings can move towards and away from each other along longitudinal axes of the rods for a given distance defined by a length of the rods, but cannot rotate with respect to each other. For example, the attachment device can include a set of at least three screws or bolts that are slidably received within respective through-holes in the bottom housing and are fixedly secured via respective threaded holes in the top housing such that the top and bottom housings cannot be rotated with respect to each other and cannot be removed from each other, and can move towards and away from each other along longitudinal axes of the at least three screws or bolts.

In certain implementations, the attachment mechanism on the upper side of the top housing includes a series of two or more concave grooves configured to connect to corresponding convex ridges on a laryngoscope handle and/or the attachment mechanism on the lower side of the bottom housing includes a series of two or more convex ridges configured to connect to corresponding convex ridges on a laryngoscope suspension arm.

In some embodiments, the systems further include a feedback system. For example, the feedback system can be configured to provide to a user any one or more of an audible alert, a visible alert, and a tactile alert corresponding to a pre-selected force threshold. In some implementations, the feedback system includes a mechanical limiter that prevents the user from applying force on a tissue beyond a specific threshold force.

In another aspect, the disclosure provides automated methods of performing a procedure using a medical device. These methods include arranging a force measurement device, e.g., a load cell, between a handle, holding system, or suspension system and a medical device to measure forces applied between the medical device and the handle, holding system, or suspension system; measuring a force applied to the force measurement device and providing a signal that indicates the force applied to one or more tissues contacted by the medical device during the procedure; analyzing the signal of force applied to the one or more tissues; and providing an output indicating a force applied to a tissue by the medical device over time, wherein the output is based on the analysis of the signal during the procedure.

In these methods, the medical device can be, for example, a laryngoscope and the procedure can be intubation or laryngoscopy, such as direct laryngoscopy (DL), microlaryngoscopy (ML), or suspension microlaryngoscopy (SML), and the tissue is laryngeal tissue. In some implementations, the methods can further include repositioning the medical device to reduce a force applied to the tissue based on the output.

The disclosure also provides systems as described herein for use in any of the methods described herein.

Additional applications include using the devices to measure the forces delivered to tissues during the design and testing of new medical devices such as laryngoscopes and other surgical instruments as well as in training and simulation environments.

The new systems and applications described herein can be extrapolated to various forms of laryngoscopy and other surgeries and medical procedures where a significant amount force is exerted onto different tissue and anatomical landmarks in a patient, e.g., in the head and neck. The TFS devices can also be used to compare pressure distributions across various medical device designs and allow for more targeted development of future instruments.

The quantification and data from these TFS devices can be used to affect several patient outcome metrics directly. Notably, the studies, as discussed below, demonstrate the predictive value of the new systems and methods for the development of both post-operative complications and peri-operative narcotic requirements. With appropriate use and implementation, these TFS systems and methods have the ability to reduce or mitigate post-operative complications and help reduce or eliminate the need for post-operative narcotics.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 11A-11D are a series of quartile boxplots that show quartile ranges for various force and time measurements, based on development of Post-Op tongue symptoms and abnormal Post-Op EAT-10 scores.

Like reference symbols in the various drawings indicate like elements.

DETAILED DESCRIPTION

The present disclosure describes the design and implementation of novel force measurement devices, the tissue force sensor (TFS), for example a laryngeal force sensor (LFS), which can be easily attached to a handle, holder system, or suspension mechanism for a medical device such as a laryngoscope, and provides dynamic feedback data (measurements in metric or imperial units) regarding the force applied to the mouth, jaws, tongue, and throat during direct laryngoscopy, such as during SML procedures. This data is displayed in real-time on a laptop or monitor next to the surgeon, actively displaying how much force is being applied to the in vivo tissues. In addition, the systems can provide audible, visible, and/or tactile signals, e.g., alarms, to alert the surgeon once a certain threshold of force has been reached, indicating a potential increased risk for post-operative complications.

The in vivo use of the new TFS, e.g., LFS, improves the safety of various medical procedures, e.g., SML and other medical procedures, e.g., in the head and neck, that involve the intentional or inadvertent manipulation of tissue in the body with a medical device that is supported or held by a handle, support system, and/or suspension mechanism to support medical device, e.g., surgical or other instruments, in terms of technique, duration, etc. during the procedures.

The new systems have been used in a prospective clinical trial on over 90 patients undergoing direct laryngoscopy. The results indicate that several measurements (maximal force and impulse) correlate with post-operative pain, tongue symptoms, and swallowing complications. The LFS device is not directly in contact with the patient and is designed primarily as a safety device to reduce post-operative pain and complications. The empirical data collected shows that the sensor is reliable and safe for use during suspension microlaryngoscopy.

Components of the TFS System

Figure 2:
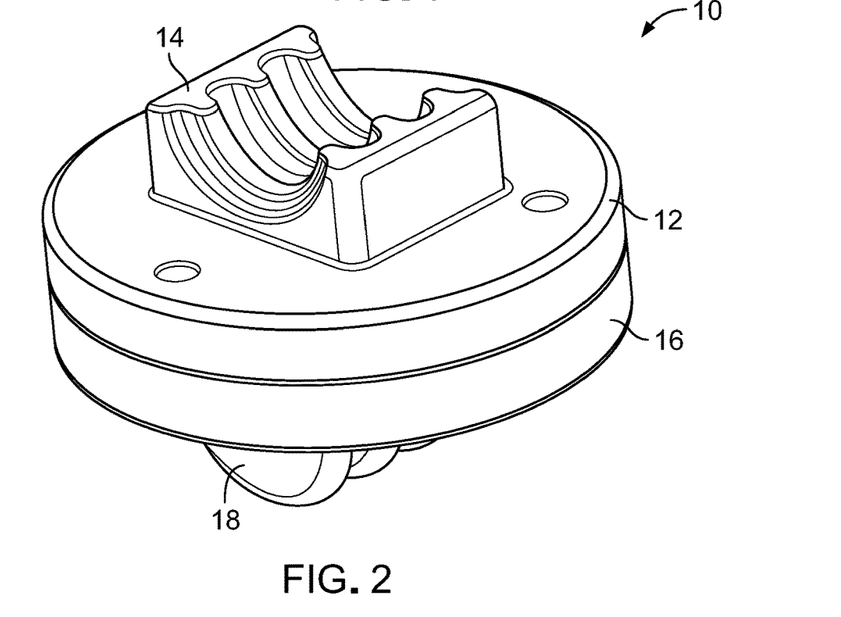
FIG. 2 is a schematic diagram of an assembled view of one embodiment of an LFS device with a top housing (dark gray) having an attachment mechanism for a laryngoscope housing and a bottom housing with an attachment mechanism for connecting to a suspension arm (light gray).
Figure 3:
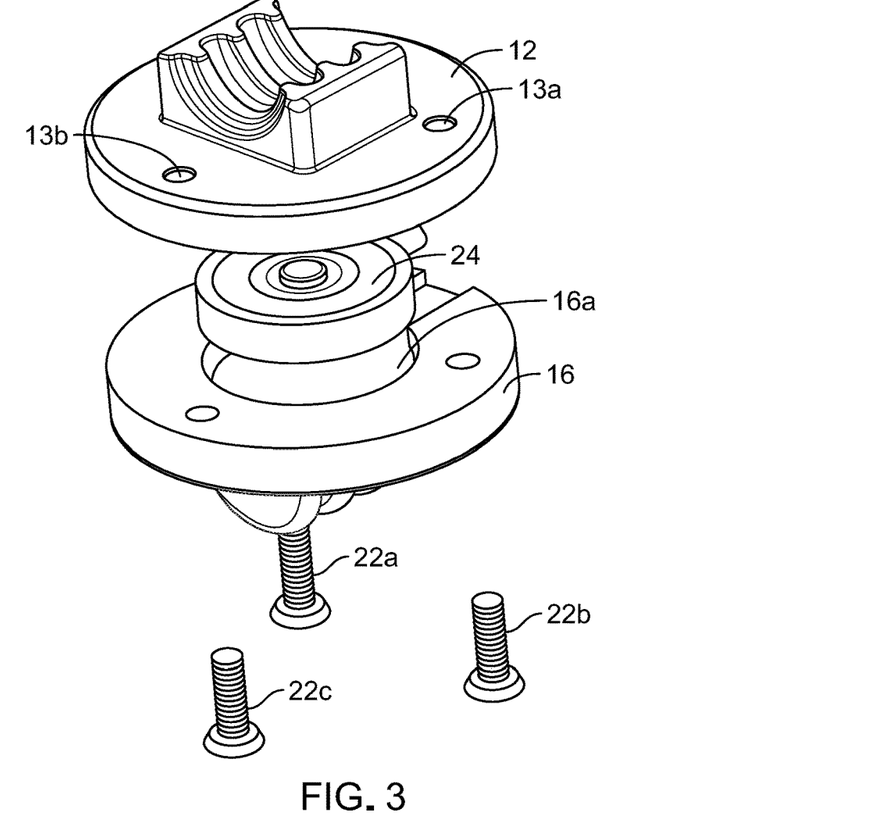
FIG. 3 is an exploded schematic view of an LFS device with capacitive load cell shown between the top (dark gray) and bottom (light gray) housings.
Figure 4:
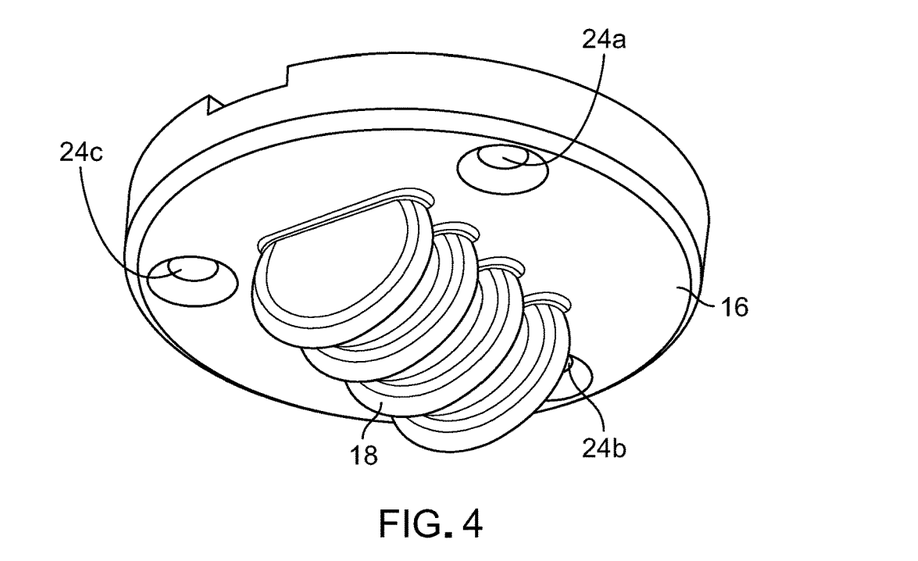
FIG. 4 is a schematic diagram of the lower side of the bottom housing of one embodiment of an LFS device.
Figure 5:
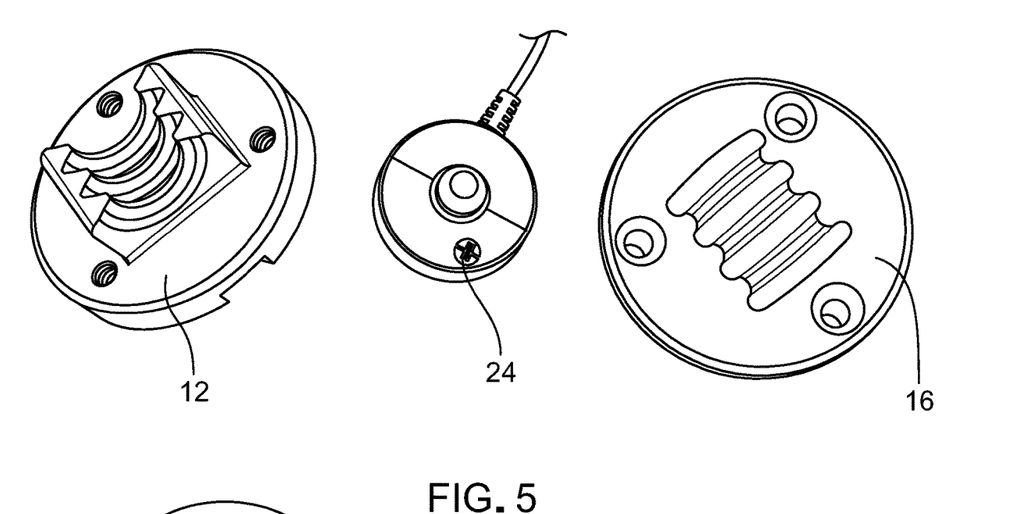
FIG. 5 is a representation of the upper side of the top housing (left side) and lower side of the bottom housing (right side) of the LFS device opened with the load cell shown in the middle.
Figure 6:
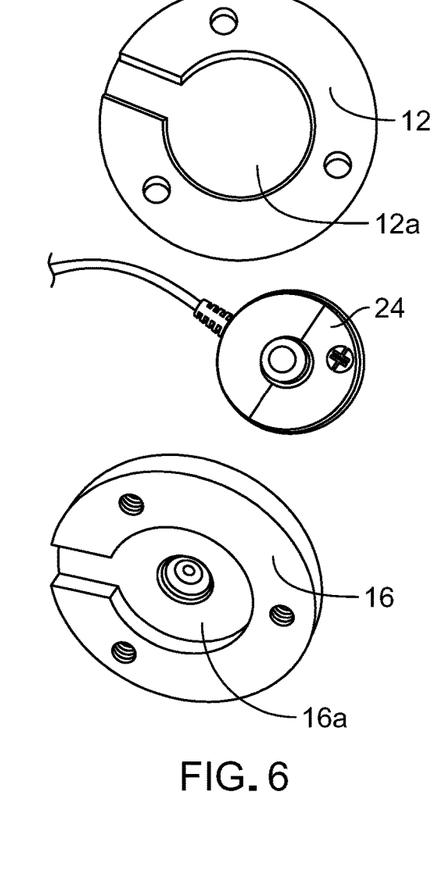
FIG. 6 is a representation of the upper side of the bottom housing (top of image) showing a cavity to receive the load cell (shown in the middle of the figure), and the lower side of the top housing (bottom of image) showing a cavity to receive the load cell.

The TFS, e.g., LFS, is an adjunct device for use in medical procedures that involve tissue manipulation, such as DL or SML, and other procedures and consists of three primary components—a top housing (shown in dark gray in FIGS. 2, 3, and 7), a bottom housing (shown in light gray in FIGS. 2, 3, 4, and 7), and a capacitive load cell sandwiched in between (shown in FIGS. 3, 5, and 6). The assembled TFS, e.g., LFS, as it would appear in suspension and in use with a patient undergoing DL is shown in FIG. 1.

Figure 1:
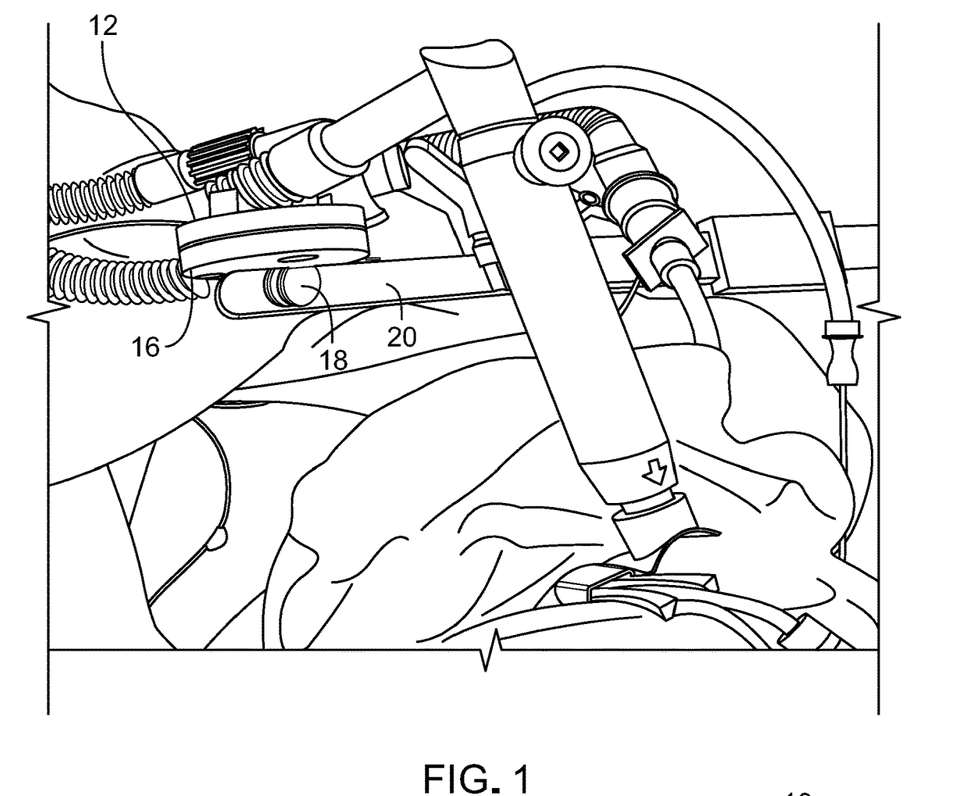
FIG. 1 is a representation of the laryngeal force sensor (LFS) device in use with a patient attached to a suspension arm at the bottom and to a laryngoscope at the top. The laryngoscope is entering the patient at the lower right side of the image (where the arrow on the laryngoscope is pointing downwards.
Figure 7:
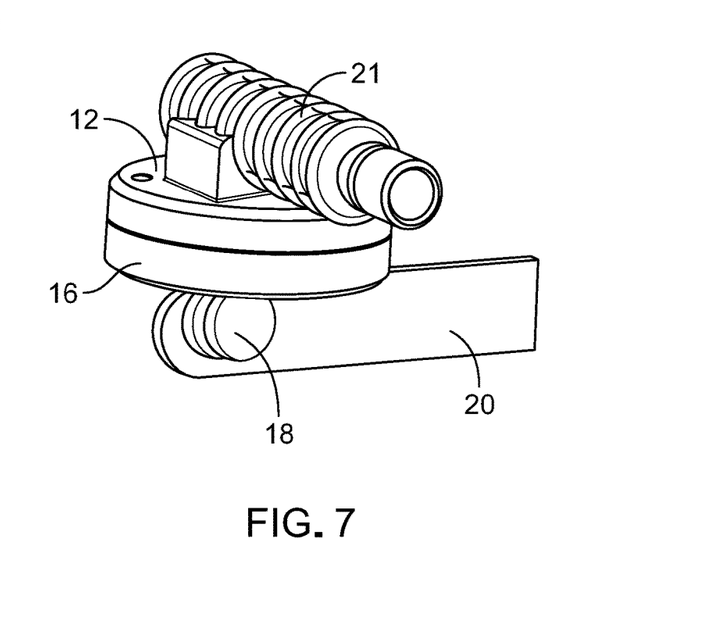
FIG. 7 is a schematic diagram of the LFS device top housing (dark gray) mounted onto the handle of a laryngoscope and bottom housing (light gray) connected to a distal arm of a laryngoscope suspension.

As shown, for example, in FIGS. 1, 2 and 7, the LFS device 10 includes top housing component 12 that has an attachment mechanism 14 on its upper side designed to fit the anterior handle attachment of a laryngoscope or other medical/surgical device 21. As shown, for example, in FIGS. 1, 2, and 4, the bottom housing component 16 includes an attachment mechanism 18 designed to fit the distal end of various suspension mechanisms 20 that are used to support laryngoscopes or other devices, e.g., during surgery.

As shown in FIG. 3, the top housing 12 and bottom housing 16 are held together with an attachment device for slidably connecting the top and bottom housings, e.g., a set of screws or bolts, e.g., three bolts 22a-c shown in FIG. 3. A load cell 24 is sandwiched between the top and bottom housings.

As show in FIG. 4, the bottom housing 16 can include recesses 24a-c to receive the heads of the bolts 22a-c. The bolts are sized to slide within through-holes cut through the bottom housing 16 and have threaded ends that engage threaded holes 13a-c in the top housing, as shown in FIG. 3. The bolt heads cannot pass through the holes, and thus when the LFS is assembled the screws or bolts are passed through the holes in the bottom housing and are secured in the top housing, thereby preventing the top and bottom housings from being separated from each other, and also preventing rotation of the top housing with respect to the bottom housing.

In other embodiments, the attachment mechanism includes one or more, e.g., 2, 3, or 4, or more, rigid rods that are slidably secured to either the top or bottom housing and rigidly secured to the other housing, to allow the top and bottom housings to move towards and away from each other along the longitudinal axes of the rods for a given distance, but cannot rotate with respect to each other or be pulled apart or separated from each other.

As shown in FIGS. 3 and 6, both the top housing 12 and the bottom housing 16 include a cavity 12a, 16a to receive the load cell. In particular, the top housing 12 includes a first cavity 12a on its lower side for receiving a top portion of a load cell, and the bottom housing 16 includes a second cavity 16a on its upper side for receiving a bottom portion of a load cell. The first and second cavities 12a, 16a are sized such that the top and bottom housings do not come into contact with each other when a load cell 24 is arranged within the first and second cavities. For example, each cavity is designed to have a depth that is slightly less than one-half of the height of the corresponding load cell 24. That way, when the load cell 24 is inserted into the first and second cavities 12a, 16a and the top housing 12 and bottom housing 16 are secured to each other with the bolts or screws 22a-c, the lower side of the top housing does not contact the upper side of the bottom housing. The depths of the first and second cavities are also designed so that even when the load cell is completely compressed, the top and bottom housings cannot touch.

All machined components are made from medical grade metals, such as 316 stainless steel or polished aluminum. The components are designed to accommodate production with a computer numerical control (CNC) mill and lathe such that more expensive fabrication methods such as die-casting or injection molding are not required, but can be used.

The new devices are robust and reliable and can be easily attached to a suspension mechanism for a laryngoscope or similar device. The machined device is designed to have appropriate dimensions and tolerances to fit with both typical laryngoscopes and suspension mechanisms. To ensure a purely axial load measurement, care is taken to provide the load cell with an appropriate clearance fit. These dynamic force measurements are also accurate and reliable throughout the SML procedures with minimal background noise.

Data Acquisition and Analysis Systems

Figure 8:
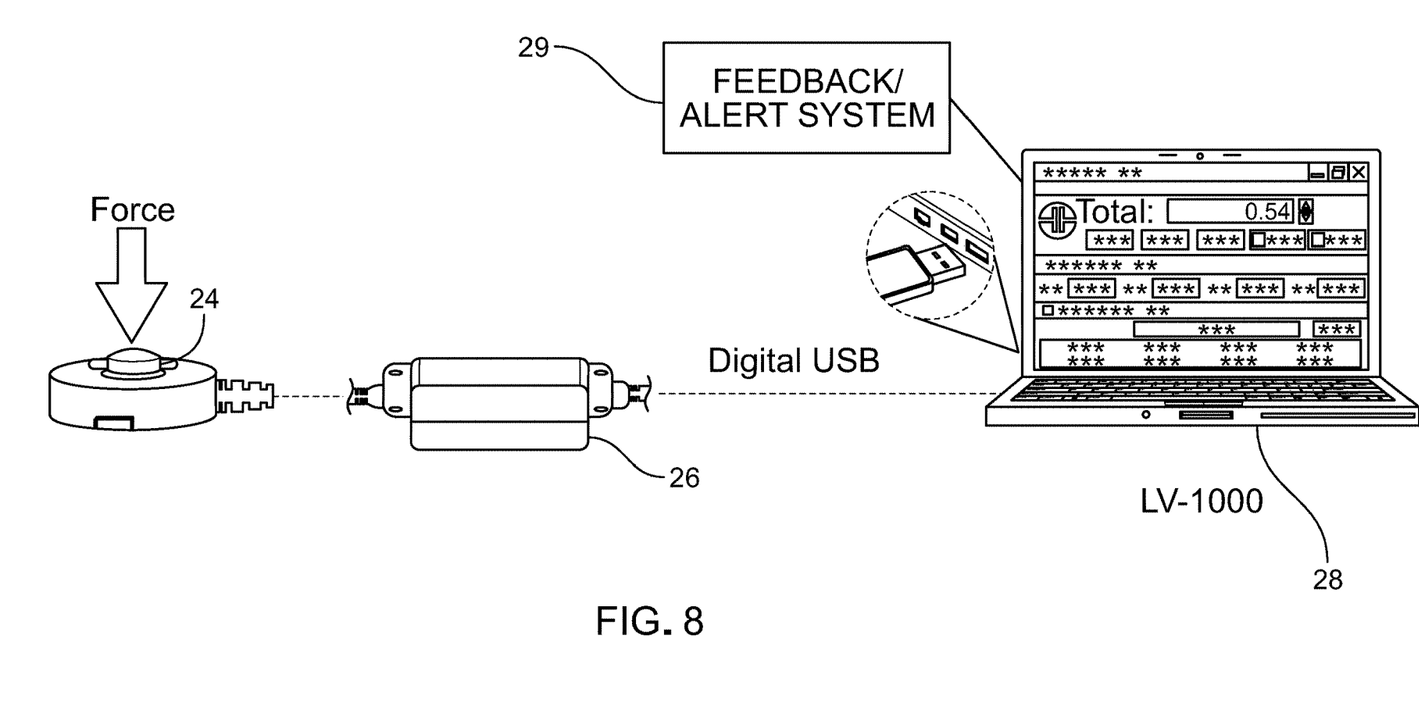
FIG. 8 is a schematic diagram of a load cell, data acquisition module, data capture software loaded onto a processor (laptop computer in this embodiment) depicted in series and a feedback/alert system linked to the processor.

FIG. 8 provides a schematic overview of how the load cell, data acquisition system, a data analysis processor, and a feedback/alert system 29 are arranged. The load cell 24, data acquisition system 26, and software on a processor 28 are all known components and are commercially available, e.g., from Loadstar Sensors, Inc. (Fremont, Calif.). The feedback/alert system 29 is also a known component or can be easily assembled from known components. All of these components can be assembled and mounted together with the custom components described herein. The load cell 24 should be rated up to at least about 200 lbs of force and be designed to measure compressive force inputs. The load cell, such as an iLoad® Mini Dome®, is connected to a data acquisition module 26, such as a single frequency channel DQ-1000U® data acquisition module (Loadstar), which converts the frequency output of the load cell to a digital USB output. The USB output is carried through USB cable or is delivered wirelessly to the processor 28, which includes software, e.g., LV-1000® (Loadstar), to analyze the digital USB output. The software is designed to plot force measurements in real-time at a frequency of up to 150 Hz.

Measurements are recorded in real time on a separate processor, such as a laptop computer, throughout the duration of the surgery.

Feedback/Alert Systems

The new TFS systems also can be configured to provide the user with dynamic feedback data (measurements in metric or imperial units) regarding the force applied to tissue, for example, in the mouth, jaw, tongue, and/or throat during direct laryngoscopy, such as during SML procedures. This data is displayed in real-time, for example on a monitor or screen of a laptop computer 28 (as shown in FIG. 8), arranged next to the surgeon, actively displaying how much force is being applied to the in vivo tissues. The feedback data can also be used to provide various feedback safety mechanisms that are based on measurements of maximum force recorded during surgery. For example, the systems can provide audible, visual, and/or tactile (mechanical) warning signals to alert the surgeon once a certain threshold of force has been reached, indicating a potential increased risk for post-operative complications if additional force is applied.

Such audible, visual, and/or tactile alerts or signals are generated by the computer system after pre-set thresholds for force measurements have been reached and provided to the surgeon by the feedback/alert system 29 as shown in FIG. 8. These thresholds are guided by research studies described herein, wherein certain force thresholds exist, above which post-operative complications are significantly more common. Such audible signals (e.g., a beeping sound that increases in frequency and/or volume as the threshold is reached and surpassed), visible signals (e.g., a colored, e.g., red, blinking light that increase in frequency as the threshold is reached and surpassed or a green light that changes to yellow and then red as the threshold is reached and surpassed), and/or tactile signals (e.g., a vibration of the device held by the surgeon, wherein the frequency or level of the vibration increases as the threshold is reached and surpassed) are generated by the computer. These alert signals can be pre-set to include single alerts that provide the user feedback once the dynamic output has reached a certain force threshold or generate a separate alert once a certain force threshold has been reached and sustained for a pre-set amount of time.

The pre-determined force thresholds that the user chooses to implement can also be used to provide mechanical feedback to the user. In such embodiments, the system includes a mechanical device that makes it impossible for the surgeon to apply a force to a tissue that is greater than the pre-selected threshold force level. For example, by implementing a torque limiting system to the suspension arm, the force generated by the laryngoscope would only be able to achieve a maximum specified force.

EXAMPLES

The invention is further described in the following examples, which do not limit the scope of the invention described in the claims.

Example 1—Prospective Clinical Trial: Investigating Mechanical Factors Affecting Post-Operative Complications in Suspension Microlaryngoscopy (SML)

A prospective clinical trial using the LFS was performed. Participants were recruited in the pre-operative setting and followed longitudinally until their second post-operative visit. Survey questions were answered at each clinic visit along with a validated swallowing questionnaire (EAT-10) used to measure dysphagia. This study design allowed us to follow prospectively the development and resolution of post-operative tongue symptoms. Pre-operative data provided an appropriate baseline for patients, while observation from the immediate post-operative period and two post-operative clinic visits allowed us to determine the trend of symptoms.

TABLE 1

List of Clinical Study Events

Study Events

1. Pre-operative assessment: patient survey, demographics, clinical tongue assessment, Mallampati score, weight, height (BMI), interincisor distance, EAT-10 score
2. Surgery-force and time analysis
3. Recovery room post-operative check, clinical evaluation of the tongue.
4. First post-operative visit (1-2 weeks). Survey and EAT-10 score and clinical assessment of the tongue
5. Second post-operative visit (4-6 weeks). Survey/EAT-10 score and clinical assessment of the tongue Recruitment Patients between the age of 18 to 99 with plans to undergo SML at Massachusetts Eye and Ear Infirmary (MEEI) were recruited from laryngology clinic to be enrolled in the study. The dropout rate was not anticipated to be significant as there was no additional burden on study participants and no change to the standard of care. With a minimal expected dropout rate, the study was approved for enrollment of 200 patients with over 90 patients having completed the study to date.

Computer and Data Analysis Systems LoadVUE® Pro (LoadStar Sensors) software was used in conjunction with the force sensor data acquisition system to capture real-time force loading measurements. The computer was encrypted to meet compliance standards to contain patient health information (PHI).

A DQ-1000U® (LoadStar Sensors) single channel frequency converter data acquisition system was used to convert the frequency output of the force sensor into a USB digital output for real-time recording.

Figure 9:
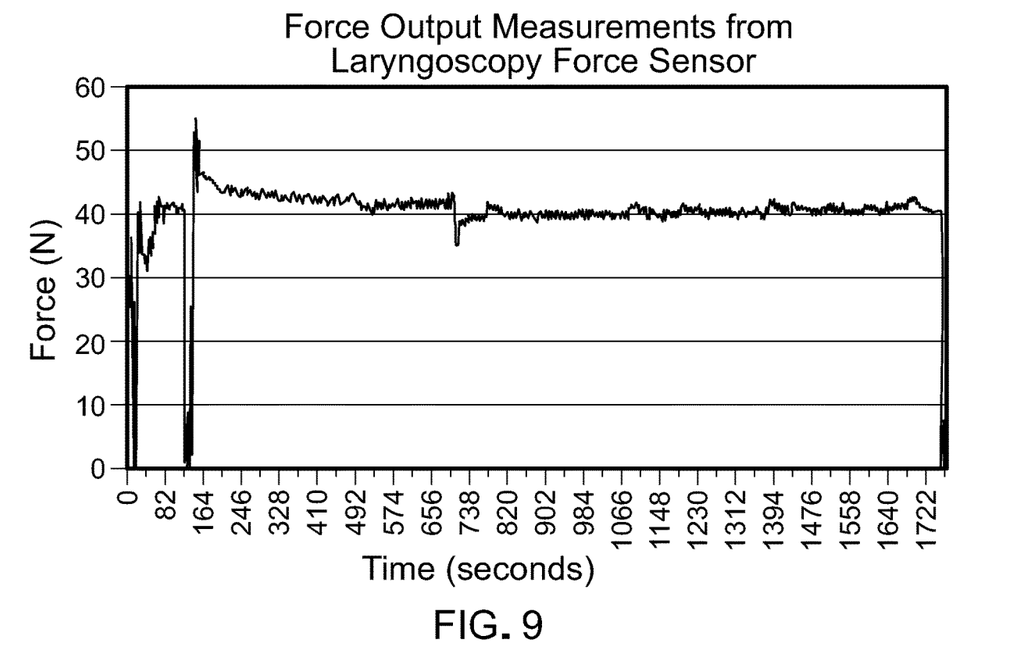
FIG. 9 is a graph that demonstrates the typical force output of the LFS device with the x-axis representing time elapsed and the y-axis representing force. This representative graph from one of the study patients demonstrates the initial elevation in pressure as the operator performs the laryngoscopy and places the device in suspension. These output readings are dynamic over the duration of the procedure and captured throughout.

A typical output from the force sensor is shown in the graph of FIG. 9. This representative graph is from the testing on one of the study patients and demonstrates the initial elevation in pressure as the operator performs the laryngoscopy and places the device in suspension. These output readings are dynamic over the duration of the procedure and captured throughout surgery.

Figure 10:
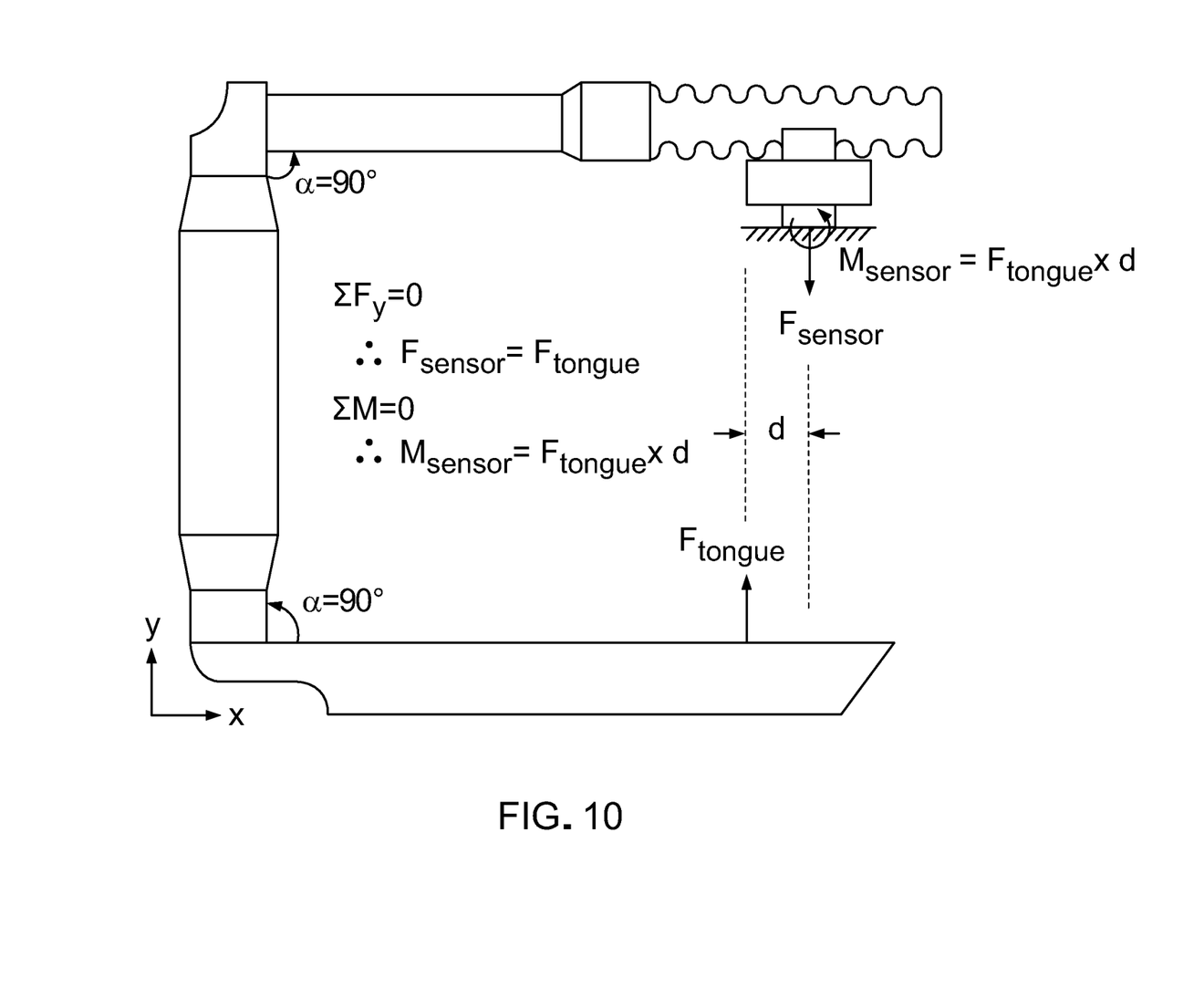
FIG. 10 is schematic free-body diagram of the LFD device mounted to a universal glottiscope. The force vectors demonstrate the axial nature of the load bearing force experienced by the LFS.

FIG. 10 illustrates a free-body diagram of the LFS mounted to a universal glottiscope. The force vectors in this figure demonstrate the axial nature of the load bearing force experienced by the LFS.

Pre and Post-Operative Clinic Visits

At recruitment in the pre-operative clinic visit, several patient factors were recorded after enrolling a patient. These include typical patient demographics (age, sex, weight, height, BMI), Mallampati score, inter-incisor distance, a clinical evaluation of the tongue, and a validated EAT-10 score (Table 2) to determine dysphagia (see, e.g., Belafsky et al., Ann. Otol. Rhinol. Laryngol., 117(12):919-24, 2008).

TABLE 2

Eating Assessment Tool (EAT-10) Survey

| Eating Assessment Tool (EAT-10) To what extent are the following scenarios problematic for you? | 0 = No problem 4 = Severe problem | | | | |
|---|---|---|---|---|---|
| 1. My swallowing problem has caused me to lose weight | 0 | 1 | 2 | 3 | 4 |
| 2. My swallowing problem interferes with my ability to go out for meals | 0 | 1 | 2 | 3 | 4 |
| 3. Swallowing liquids takes extra effort | 0 | 1 | 2 | 3 | 4 |
| 4. Swallowing solids takes extra effort | 0 | 1 | 2 | 3 | 4 |
| 5. Swallowing pills takes extra effort | 0 | 1 | 2 | 3 | 4 |
| 6. Swallowing is painful | 0 | 1 | 2 | 3 | 4 |
| 7. The pleasure of eating is affected by my swallowing | 0 | 1 | 2 | 3 | 4 |
| 8. When I follow food sticks in my throat | 0 | 1 | 2 | 3 | 4 |
| 9. I cough when I eat | 0 | 1 | 2 | 3 | 4 |
| 10. Swallowing is stressful | 0 | 1 | 2 | 3 | 4 |
| Total EAT-10 Score | | | | | |

The clinical evaluation of the tongue included assessment of tongue deviation, assessment of tongue dysguesia, and assessment of tongue paresthesia. This clinical evaluation was also performed on post-operative day 0 in the recovery room, on the first post-operative visit (approximately 1-2 weeks after surgery), and on the second post-operative visit (approximately 4-6 weeks after surgery). Patient survey questions (Table 3) were also given during these post-operative periods. The patient tongue survey consists of a 4-point Likert scale assessing subjective change in taste, numbness, and pain after undergoing SML. The presence of tongue paresis after surgery was also recorded during the post-operative period.

TABLE 3

Patient Tongue Survey Questions Regarding Change in Taste, Numbness, and Pain

| Question | Absent | Mild | Moderate | Severe |
|---|---|---|---|---|
| My change in taste is | 0 | 1 | 2 | 3 |
| My tongue numbness is | 0 | 1 | 2 | 3 |
| My tongue pain is | 0 | 1 | 2 | 3 |

Example 2—Clinical Study 1: Quantifying Extralaryngeal Complications after Suspension Microlaryngoscopy (SML)

The LFS device was used throughout SML cases across a wide variety of indications to determine whether a correlation exists between force loadings and post-operative tongue complications. Several different metrics were investigated including maximum force, average force, total suspension time, and the total impulse experienced throughout surgery for the first 56 patients to complete the study. This study and the results are also reported in Feng et al., "Laryngeal Force Sensor: Quantifying Extralaryngeal Complications after Suspension Microlaryngoscopy," Otolaryngol. Head Neck Surg., Epub ahead of print, PMID: 29613830 (2018), which is incorporated herein by reference in its entirety.

Statistical Analysis

Data was analyzed using STATA 13.0 (StataCorp, College Station, Tex.) with significance attributed to p-values <0.05. A change or development in tongue related symptoms from the pre-operative period to the post-operative period was investigated along with the development of an abnormal EAT-10 score. This was defined as a post-operative EAT-10 score of 3 or greater (patients with abnormal pre-operative EAT-10 scores were not included)(Jahn et al., Logoped. Phoniatr. Vocol., 21(3-4): 181-5, 1996). Associations with nominal variables were analyzed using cross tabulations and Fisher's exact test whereas analysis of variance was used to analyze associations with continuous variables. A stepwise backward variable selection approach was used to build sequentially the regression model with average marginal effects reported for significant variables. A multiple logistic regression was performed to identify factors associated with our binary outcome metrics.

Results

Of the 56 patients in the final analysis for this initial study (Feng et al. 2018), 27 were male (48%) and 29 were female (52%). The median age was 58 years (range, 19-83 years). Study patients had an average BMI of 27.8 (range, 19.2-42.3) and Mallampati score of 1.79 (range, 1-3). The majority of these cases were for benign indications (75%) whereas the remainder was for malignancy (25%). Some form of laser—KTP, $CO_2$ or both—was used in the majority of cases (57%). The mean maximum force recorded across all patients was 164.7 N (95% CI: 141.0-188.4 N, range: 48.5-402.6 N) and the mean average force for all patients was 92.0 N (95% CI: 76.9-107.1 N, range: 10.0-231.4 N). The mean suspension time for all patients was 34.3 minutes (95% CI: 27.4-41.2 min, range: 7.1-108.1 min) and the average total impulse experienced by each patient during suspension was 172.3 kN·s (95% CI: 124.0-220.6 kN·s, range: 3.4-108.4 kN·s). Values for these force measurements and suspension times are summarized in Table 4.

TABLE 4

Patient Variables and Their Relationship to the Development of Postoperative Tongue Symptoms and Abnormal EAT-10 Scores

| | Postoperative Tongue Symptoms | | Postoperative Abnormal EAT-10 | |
|---|---|---|---|---|
| Force Measurement | Mean (SD) | P Value | Mean (SD) | P Value |
| Maximum force, N (n = 56) | 164.7 (11.8) | | 164.7 (11.8) | |
| Patients without complications | 122.7 (53.8) | <.001 | 143.0 (75.1) | .001 |
| Patients with complications | 240.3 (89.6) | | 229.7 (96.8) | |

TABLE 4-continued

Patient Variables and Their Relationship to the Development of
Postoperative Tongue Symptoms and Abnormal EAT-10 Scores

| Force Measurement | Postoperative Tongue Symptoms | | Postoperative Abnormal EAT-10 | |
|---|---|---|---|---|
| | Mean (SD) | P Value | Mean (SD) | P Value |
| Average force, N (n = 56) | 92.0 (7.5) | | 92.0 (7.5) | |
| Patients without complications | 72.8 (45.6) | <.001 | 82.2 (52.9) | .022 |
| Patients with complications | 126.6 (58.3) | | 121.5 (57.7) | |
| Suspension time, min (n = 56) | 34.3 (3.4) | | 34.3 (3.4) | |
| Patients without complications | 29.5 (20.8) | .060 | 33.3 (25.9) | .622 |
| Patients with complications | 43.0 (31.7) | | 37.3 (26.1) | |
| Total impulse, kN · s (n = 56) | 172.3 (24.1) | | 172.3 (24.1) | |
| Patients without complications | 114.9 (111.6) | <.001 | 153.9 (187.6) | .188 |
| Patients with complications | 275.7 (231.7) | | 227.6 (148.9) | |

Abbreviation: EAT-10, 10-item Eating Assessment Tool.

The majority of patients did not experience any tongue related complications immediately after surgery. After surgery, 20 patients (36%) experienced development of at least one symptom of tongue dysguesia, paresthesia, pain, or paresis compared to their pre-operative baseline. Eleven patients (20%) experienced a mild increase in one tongue related symptom, 8 patients (14%) experienced a mild increase in two tongue related symptoms, and 1 patient (2%) experienced a mild increase in three tongue related symptoms. No patients experienced moderate or severe increase in tongue related symptoms following surgery. Of the 56 patients enrolled in the study, 12 patients (21%) developed an abnormal EAT-10 score after surgery compared to their normal EAT-10 baseline (score greater than 3). These results are summarized in Table 5.

TABLE 5

Occurrences for Tongue-Related Symptoms and
Development of Abnormal EAT-10 Scores

| Complication | Occurrences, n (%) |
|---|---|
| Tongue symptoms | 20 (36) |
| Dysgeusia | 6 (11) |
| Paresthesia | 10 (18) |
| Pain | 9 (16) |
| Paresis | 5 (9) |
| Abnormal EAT-10 score | 12 (21) |

Abbreviation: EAT-10, 10-item Eating Assessment Tool.

Figure 11A:
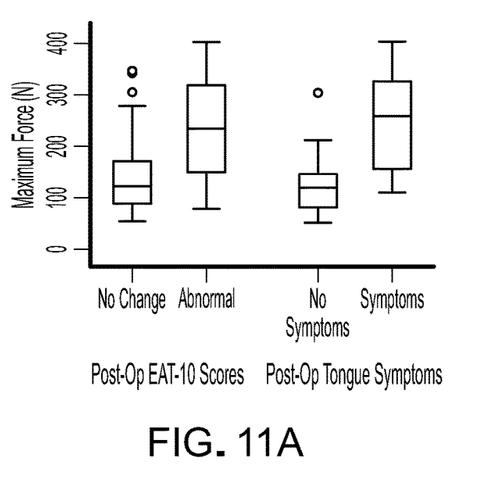
FIG. 11A shows maximum force.
Figure 11B:
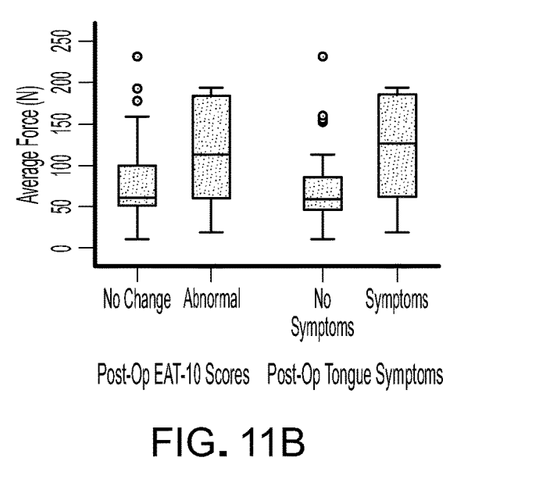
FIG. 11B shows average force.
Figure 11C:
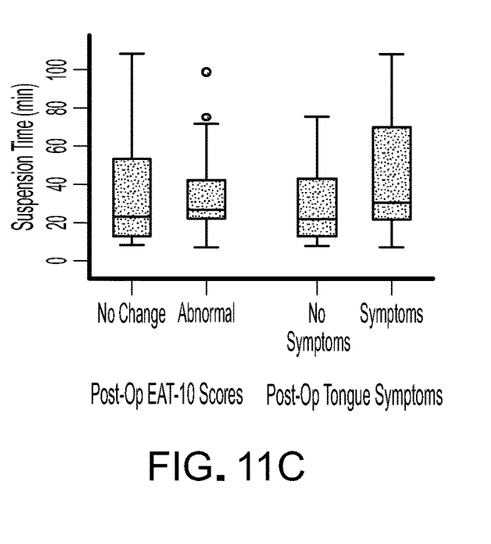
FIG. 11C shows suspension time.
Figure 11D:
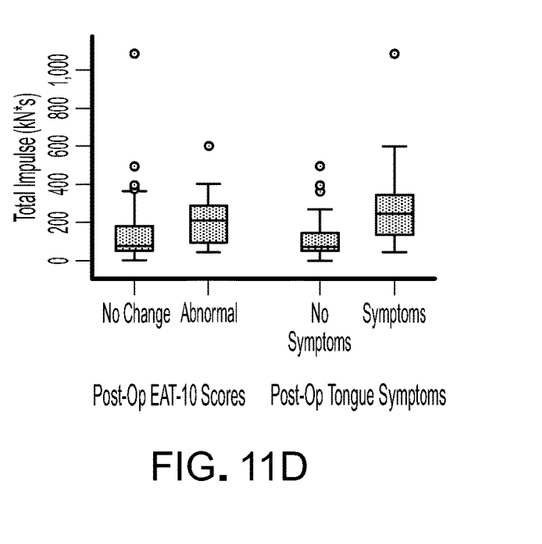
FIG. 11D shows total impulse.

On univariate analysis, no patient variables were associated with the development of post-operative tongue symptoms or an abnormal EAT-10 score. The maximum force, average force, and total impulse experienced during surgery were significantly correlated with development of post-operative tongue symptoms (p<0.001). Both maximum force (p=0.001) and average force (p=0.022) were significantly associated with the development of an abnormal EAT-10 score post-operatively. These results are summarized in Table 4 and quartile ranges for these force measurements, based on development of tongue symptoms and abnormal EAT-10 scores, are shown in FIGS. 11A-11D. In particular, FIG. 11A shows maximum force, FIG. 11B shows average force, FIG. 11C shows suspension time, and FIG. 11D shows total impulse.

A generalized linear model with logistic regression was performed to assess predictor values for the development of tongue symptoms after SML. After controlling for other possible cofounding variables, maximum force experienced during the procedure (OR 1.15, 95% CI: 1.02-1.29, p=0.019) and sex were significant predictors for developing post-operative tongue symptoms. From post-estimation analysis of margins, female patients were 30.1% (95% CI: 22.7-37.5%, p<0.001) more likely to experience post-operative tongue symptoms. These findings are summarized in Table 6.

TABLE 6

Generalized Linear Model with Logistic Regression for Variables
Associated with Development of Postoperative Tongue Symptoms

| Variable | Odds Ratio | 95% Confidence Interval | p-value |
|---|---|---|---|
| Post-Op Tongue Symptoms | | | |
| Maximum Force | 1.1492 | 1.0236-1.2902 | 0.019 |
| Average Force | 0.9385 | 0.8337-1.0564 | 0.293 |
| Suspension Time | 1.2238 | 0.9158-1.6354 | 0.172 |
| Total impulse | 1.0069 | 0.9703-1.0449 | 0.714 |
| Age | 0.9566 | 0.8451-1.0827 | 0.482 |
| BMI | 1.0236 | 0.7345-1.4265 | 0.89 |
| Male | ref | | |
| Female | 21166 | $1.4824\text{-}3.02 \cdot 10^5$ | 0.041 |
| Benign | ref | | |
| Malignant | 0.00003 | $3.37 \cdot 10^{-11}\text{-}26.0308$ | 0.135 |
| No laser | ref | | |
| KTP only | 0.3672 | 0.0064-21.2060 | 0.628 |
| CO2 ± KTP laser | 0.0025 | $2.40 \cdot 10^5\text{-}2.6811$ | 0.092 |
| Left sided lesion | ref | | |
| Right sided lesion | 0.1613 | 0.0007-50.3972 | 0.552 |
| No sidedness | 0.0121 | 0.00002-6.0642 | 0.164 |
| Mallampati I | ref | | |
| Mallampati II | 0.4952 | 0.0040-60.7454 | 0.775 |
| Mallampati III | 35.929 | 0.2610-4946.85 | 0.154 |

For development of abnormal post-operative EAT-10 scores, the only significant predictor was the maximum force experienced during the procedure (OR 1.03, 95% CI: 1.00-1.06, p=0.045). These findings are summarized in Table 7. Other patient characteristics and force measurements including age, BMI, Mallampati score, average force, total suspension time, and total impulse were not significant predictors for the development of tongue symptoms or an abnormal EAT-10 score.

TABLE 7

Generalized Linear Model with Logistic Regression for Variables Associated with Development of Postoperative Abnormal EAT-10 Scores

| Variable | Odds Ratio | 95% Confidence Interval | p-value |
|---|---|---|---|
| Post-Op Abnormal EAT-10 | | | |
| Maximum Force | 1.0301 | 1.0007-1.0603 | 0.045 |
| Average Force | 1.0008 | 0.9479-1.0567 | 0.977 |
| Suspension Time | 1.0402 | 0.9545-1.1336 | 0.369 |
| Total impulse | 0.9942 | 0.9821-1.0064 | 0.350 |
| Age | 0.9917 | 0.9324-1.0546 | 0.790 |
| BMI | 1.0890 | 0.9131-1.2989 | 0.343 |
| Male | ref | | |
| Female | 6.4928 | 0.5020-83.9704 | 0.152 |
| Benign | ref | | |
| Malignant | 0.0240 | 0.0004-1.3144 | 0.068 |
| No laser | ref | | |
| KTP only | 3.1600 | 0.2000-49.9394 | 0.414 |
| CO2 ± KTP laser | 5.2889 | 0.1429-195.753 | 0.366 |
| Left sided lesion | ref | | |
| Right sided lesion | 4.9448 | 0.1734-140.989 | 0.350 |
| No sidedness | 0.1600 | 0.0067-2.9591 | 0.218 |
| Mallampati I | ref | | |
| Mallampati II | 0.7423 | 0.1073-5.1372 | 0.763 |
| Mallampati III | 0.2464 | 0.0083-7.3110 | 0.418 |

Our results show that an increased maximum force during SML procedures is predictive of both increased post-operative complications and development of an abnormal EAT-10 score, a marker for dysphagia. These findings are significant and provide the surgeon with valuable information regarding optimal positioning to minimize intra-operative forces and total impulses during surgery to prevent these complications. By specifically minimizing the maximum force during surgery, surgeons may be able to eliminate the development of these post-operative complications (pain, paresthesia, paresis, dysguesia) or dysphagia. Even in the event of unavoidably high force distributions, this information would provide valuable insight towards optimal and efficient postoperative care (i.e., appropriate narcotic prescriptions, symptom monitoring and diet, etc.).

Example 3—Clinical Study 2: Laryngeal Force Sensor Metrics are Predictive of Increased Perioperative Narcotic Requirements After demonstrating the value of LFS force metrics in predicting the development of postoperative complications including pain, we sought to investigate the correlation between these metrics and perioperative narcotic requirements. In this follow up study, intraoperative and postoperative narcotic use was tabulated and converted to morphine equivalents (mg). To this point, a total of 82 patients had completed the study.

Statistical Analysis

Data was analyzed using STATA 13.0 (StataCorp, College Station, Tex.) with significance attributed to p-values <0.05. Narcotic use in terms of morphine equivalents (ME) was investigated to determine the relationship between patient variables and measured force metrics. Comparisons between different groups of nominal variables were analyzed using one-way analysis of variance. Pearson's correlation coefficient and linear regression were performed for measurement variables. All variables were assumed to be normally distributed and homoscedastic. A stepwise backward variable selection approach was used to build sequentially the regression model. A multiple linear regression was performed to identify factors associated with perioperative narcotic use.

Results

Of the 82 patients in the final analysis, the average perioperative narcotic requirement in terms of IV morphine equivalents (ME) was 16.96 mg (95% CI: 14.3-19.80 mg, range: 0.15-79.82 mg). On univariate analysis with individual patient factors, there was a significant difference between patients of differing BMI categories (p=0.047), with those of normal BMI requiring on average 11.79 mg of ME, overweight patients requiring 17.99 mg of ME, and obese patients requiring 20.68 mg of ME. Similarly, those who had malignancies had an average requirement of 24.69 mg compared to 15.09 mg for benign indications (p=0.007). Patients who did not require KTP or CO2 laser during their case had an average requirement of 11.04 mg of ME compared to 22.33 mg for those who did (p<0.001). Notably, multiple force metrics were recorded with the LFS that were significantly correlated with perioperative narcotic requirements. The correlation with perioperative narcotic requirements for both total suspension time (r=0.526, p<0.001) and total impulse (r=0.295, p=0.007) were significant on univariate analysis. These results are shown in Table 8.

TABLE 8

Recorded Force Measurements and Their Relationship to Perioperative Narcotic Requirements on Univariate Analysis

| | | Perioperative Narcotic Requirements | | |
|---|---|---|---|---|
| LFS Measurements | Mean (SD) | Pearson's r | 95% CI | P Value |
| Maximum Force (n = 82) | | | | |
| SI Units (N) | 166.1 (87.1) | 0.127 | (−0.093)-0.334 | 0.257 |
| Imperial Units (lbf) | 37.3 (19.6) | | | |
| Average Force (n = 82) | | | | |
| SI Units (N) | 93.5 (53.5) | −0.055 | (−0.270)-0.160 | 0.624 |
| Imperial Units (lbf) | 21.0 (12.0) | | | |
| Suspension Time, min (n = 82) | 33.0 (24.8) | 0.526 | 0.348-0.667 | <0.001 |

TABLE 8-continued

Recorded Force Measurements and Their Relationship to Perioperative Narcotic Requirements on Univariate Analysis

| LFS Measurements | Mean (SD) | Perioperative Narcotic Requirements | | |
| --- | --- | --- | --- | --- |
| | | Pearson's r | 95% CI | P Value |
| Total impulse (n = 82) | | | | |
| SI Units (kN · s) | 170.6 (174.7) | 0.295 | 0.082-0.481 | 0.007 |
| Imperial Units (ton · s) | 19.2 (19.6) | | | |

A generalized linear model was used for the multiple linear regression to assess for predictor values associated with perioperative narcotic requirements from SML. After controlling for various patient variables and potential confounding factors, total suspension time was the only significant factor associated with perioperative narcotic use (0.273 mg/min, 95% CI: 0.040-0.507 mg/min, p=0.022). A marginal incremental increase of 0.273 mg of IV ME was seen per minute of total suspension time. Notably, this total suspension time is a representation of the true suspension time throughout surgery and accounts for any periods of relaxation during the case. This is a metric that is only attainable with the LFS force sensor. Maximum force demonstrated a trend toward significance as a possible predictive factor (0.052 mg/lbf, 95% CI: (−0.011)-0.115 mg/lbf, p=0.107). Other patient characteristics and force measurements including BMI, procedure indication, and use of laser were not significant predictors for increased perioperative narcotic requirements after SML. These results are summarized in Table 9.

TABLE 9

Generalized Linear Model for Variables Associated with the Perioperative Narcotic Requirement after Suspension Microlaryngoscopy

| Variable | Coefficient | 95% CI | P Value |
| --- | --- | --- | --- |
| Perioperative Narcotic Use | | | |
| Maximum Force (lbf) | 0.231 | (−0.050)-0.512 | 0.107 |
| Average Force (lbf) | −0.126 | (−0.713)-0.462 | 0.675 |
| Suspension Time (min) | 0.273 | 0.040-0.507 | 0.022 |
| Total impulse (ton · s) | −0.226 | (−0.546)-0.094 | 0.166 |
| Age | −0.123 | (−0.304)-0.058 | 0.184 |
| Body Mass Index | 0.206 | (−0.333)-0.744 | 0.454 |
| Sex | | | |
| Male | Ref | | |
| Female | −1.332 | (−7.170)-4.507 | 0.655 |
| Indication | | | |
| Benign | Ref | | |
| Malignant | 4.120 | (−4.031)-12.271 | 0.322 |
| Laser | | | |
| No laser | Ref | | |
| KTP or CO2 | 4.251 | (−2.452)-10.954 | 0.214 |
| Side | | | |
| Left-sided lesion | Ref | | |
| Right-sided lesion | −4.069 | (−11.939)-3.601 | 0.311 |
| No sidedness | −1.510 | (−7.947)-4.928 | 0.646 |
| Mallampati | | | |
| I | Ref | | |
| II | 3.065 | (−2.562)-8.693 | 0.266 |
| III | 1.274 | (−6.513)-9.061 | 0.748 |

The growing opioid epidemic in the United States has been well documented, with misuse of prescription opioids playing a significant role. There has been an exponential increase in opioid use over the past two decades, with more than 60 million patients having had at least one opioid prescription filled or re-filled in 2016 (Hagemeier, "Introduction to the opioid epidemic: the economic burden on the healthcare system and impact on quality of life," Am. J. Manag. Care., 24:S200-S206, 2018). Over 11 million Americans misused opioids during that same year with over 42,000 deaths from opioid overdose (Substance Abuse and Mental Health Services Administration 2016, Center for Disease Control 2016). With such a significant impact and burden on our health care system, methods to reduce prescription narcotics are of paramount importance. Numerous studies have attempted to identify risk factors that are associated with prolonged postoperative opioid requirements or development of chronic opioid use, including preoperative substance abuse (alcohol, benzodiazepines, and opioids) or medical comorbidities like diabetes, hypertension, anxiety, depression, and fibromyalgia. This study describes the first report of a surgical monitoring technology that both correlates with postoperative pain and has the potential to predict opioid requirements.

These findings demonstrate that the force metrics measured and monitored by the LFS are significantly associated with perioperative narcotic requirements for patients undergoing SML. In particular, total suspension time was a significant predictive variable of perioperative narcotic requirements while an increase in total impulse showed a significant correlation with perioperative narcotic use. This should lead to the subsequent reduction or elimination of narcotic prescriptions in select patients, an important consideration in face of our current opioid epidemic.

OTHER EMBODIMENTS

A number of embodiments of the invention have been described. Nevertheless, it will be understood that various modifications may be made without departing from the spirit and scope of the invention.

For example, the devices described herein that provide real-time force measurements can be used in conjunction with surgical instruments other than laryngoscopes during the course of operations in various surgical fields and procedures. For example, force measurements on retractors can reduce traction injuries to nerves and/or adjacent tissues. In these settings, the placement of self-retaining retractors during carotid surgery has been implicated in vagal nerve injury and the new systems and methods can help reduce these complications.

In addition, direct laryngoscopy is part of almost every general anesthesia case, and having force measurements for anesthesiologists can assist in reducing intra-oral complications and dental injuries.

Accordingly, other embodiments are within the scope of the following claims.

What is claimed is:

1. A tissue force sensor system comprising
   a top housing comprising on an upper side thereof an attachment mechanism for connecting the top housing to a medical device, and on a lower side thereof a first cavity for receiving a top portion of a force measurement device;
   a bottom housing comprising on a lower side thereof an attachment mechanism for connecting the bottom housing to a handle, holding system, or suspension system for holding or supporting the medical device and on an upper side thereof a second cavity for receiving a bottom portion of the force measurement device; and
   an attachment device for slidably connecting the top housing to the bottom housing along a central axis of the top and bottom housings, wherein the first and second cavities are sized such that the top and bottom housings do not contact each other when a force measurement device is arranged within the first and second cavities.

2. The system of claim 1, wherein the medical device is a laryngoscope, and wherein the system is configured to sense force on a laryngeal tissue.

3. The system of claim 1, further comprising a force measurement device arranged between the top and bottom housings within the first and second cavities.

4. The system of claim 3, wherein the force measurement device comprises a load cell.

5. The system of claim 3, further comprising a data acquisition system in communication with the force measurement device and a processor loaded with data analysis software in communication with the data acquisition system.

6. The system of claim 5, wherein the data acquisition system is configured to receive input signals from the force measurement device and convert those signals into digital output, and wherein the data analysis software is configured to receive the digital output over time and provide real-time force data over time.

7. The system of claim 5, wherein the force measurement device comprises a load cell.

8. The system of claim 1, wherein the top and bottom housings comprise metal.

9. The system of claim 1, wherein the attachment device comprises one or more rods that are slidably secured to either the top or bottom housing and fixedly secured to either the bottom or the top housing, wherein the top and bottom housings and rods are arranged such that the top and bottom housings can move towards and away from each other along longitudinal axes of the rods for a given distance defined by a length of the rods, but cannot rotate with respect to each other.

10. The system of claim 1, wherein the attachment device comprises a set of at least three screws or bolts that are slidably received within respective through-holes in the bottom housing and are fixedly secured via respective threaded holes in the top housing such that the top and bottom housings cannot be rotated with respect to each other and cannot be removed from each other, and can move towards and away from each other along longitudinal axes of the at least three screws or bolts.

11. The system of claim 1, wherein the attachment mechanism on the upper side of the top housing comprises a series of two or more concave grooves configured to connect to corresponding convex ridges on a laryngoscope handle.

12. The system of claim 1, wherein the attachment mechanism on the lower side of the bottom housing comprises a series of two or more convex ridges configured to connect to a laryngoscope suspension arm.

13. The system of claim 1, further comprising a feedback system.

14. The system of claim 13, wherein the feedback system provides to a user any one or more of an audible alert, a visible alert, and a tactile alert corresponding to a preselected force threshold.

15. The system of claim 13, wherein the feedback system comprises a mechanical limiter that prevents the user from applying force on a tissue beyond a specific threshold force.

* * * * *

UNITED STATES PATENT AND TRADEMARK OFFICE
CERTIFICATE OF CORRECTION

| | |
|---|---|
| PATENT NO. | : 11,564,625 B2 |
| APPLICATION NO. | : 16/645118 |
| DATED | : January 31, 2023 |
| INVENTOR(S) | : Feng et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 505 days.

Signed and Sealed this
Fourteenth Day of January, 2025

Derrick Brent
*Acting Director of the United States Patent and Trademark Office*